United States Patent [19]

Yasuda et al.

[11] Patent Number: 4,755,056
[45] Date of Patent: Jul. 5, 1988

[54] INSTRUMENT FOR SPECTROSCOPY HAVING METAL HALIDE LAMP AS LIGHT SOURCE

[75] Inventors: Makoto Yasuda, Kodaira; Tsune Miyashita, Tokyo, both of Japan

[73] Assignee: Hitachi, Ltd., Tokyo, Japan

[21] Appl. No.: 63,921

[22] Filed: Jun. 19, 1987

[30] Foreign Application Priority Data

Jun. 23, 1986 [JP] Japan ................................ 61-144936

[51] Int. Cl.⁴ ................................................ G01J 3/42
[52] U.S. Cl. ..................................... 356/51; 250/373; 313/640; 356/328
[58] Field of Search ................. 313/640, 641; 250/373; 356/51, 319, 326, 328

[56] References Cited

U.S. PATENT DOCUMENTS

| 3,452,238 | 6/1969 | Larson | 313/641 |
| 3,842,307 | 10/1974 | Dobrusskin et al. | 313/640 X |
| 4,020,377 | 4/1977 | Popp et al. | 313/571 X |
| 4,074,164 | 2/1978 | Leyendecker | 313/641 X |
| 4,229,673 | 10/1980 | McAllister | 313/640 |
| 4,647,814 | 3/1987 | Dobrusskin et al. | 313/641 |
| 4,692,883 | 9/1987 | Nelson et al. | 356/319 X |

FOREIGN PATENT DOCUMENTS 59-215654 12/1984 Japan .

Primary Examiner—F. L. Evans
Attorney, Agent, or Firm—Antonelli, Terry & Wands

[57] ABSTRACT

An instrument for spectroscopy according to this invention uses a metal halide lamp, in which at least mercury and dysprosium halide are enclosed, as the light source for the purpose of effecting measurements for a wavelength region extending from the ultraviolet to the visible light with a single light source. This metal halide lamp has a spectre, which is effective in a wavelength region extending from about 200 nm to about 700 nm.

1 Claim, 2 Drawing Sheets

INSTRUMENT FOR SPECTROSCOPY HAVING METAL HALIDE LAMP AS LIGHT SOURCE

BACKGROUND OF THE INVENTION

This invention relates to a scientific instrument for spectroscopy and in particular to a scientific instrument for spectroscopy suitably used for the ultraviolet and visible region.

In the field of the spectroscopical analysis a wide wavelength region extending from ultraviolet to visible light is used. For the light source used in an instrument by which qualitative and quantitative analysis is effected while measuring absorption of light by material, among various scientific instruments for spectroscopy, it is particularly important that fluctuations in light intensity with the time are small. However, there are in practice no single light sources having an emission spectrum extending from the ultraviolet to the visible region and small fluctuations in light intensity. As a light source having an emission spectrum in these regions there is known a xenon short arc lamp, but it is not used in practice, because its fluctuations in light intensity with the time are great. On the contrary, as light source having small fluctuations in light intensity with the time, there are known a deuterium discharge lamp and a tungsten lamp. The emission spectrum of the deuterium discharge lamp is strong in the ultraviolet region, but weak in the visible region and on the other hand, that of the tungsten lamp is strong in the visible region but weak in the ultraviolet region. For this reason these lamps cannot cover alone the wide wavelength region extending from the ultraviolet to the visible light. Consequently, in a prior art device, a construction is adopted, by which the light path is changed mechanically by means of a mirror, etc. so that as the light source a deuterium discharge lamp is used for the short wavelength side and a tungsten lamp for the long wavelength side. Therefore, it had disadvantages that the mechanism is complicated, further that since the two light paths are not coincide with each other at the wavelength, at which that light sources are changed over, measured absorption spectrum changes stepwise there, etc.

Moreover a lamp, in which a deuterium discharge lamp and a tungsten lamp are incorporated in one body so that it can be used as a light source covering the wavelength region extending from the ultraviolet to the visible light, is described in No. JP-A-59-215654. However, since the emitting point of the deuterium discharge lamp and that of the tungsten lamp are different in this lamp, it has difficulty in regulating the two emitting points on a same light axis, further that two power supplier are necessary for the deuterium discharge lamp and for the tungsten lamp, etc.

As described above, according to the prior art techniques, since there were no suitable light sources, there were problems that the instrument was complicated and expensive, that measurement result was wanting in reliability, etc.

SUMMARY OF THE INVENTION

The object of this invention is to provide an instrument for spectroscopy permitting to effect measurements for a wide wavelength region extending from the ultraviolet to the visible light with a single light source without using a plurality of light sources of different kinds, which are changed over depending on the wavelength region according to the prior art techniques.

The above object can be achieved by using a metal halide lamp filled at least with mercury and dysprosium halide as the light source.

Since the metal halide lamp described above has a spectrum, which can be efficiently utilized for a wide wavelength region extending from about 220 nm to about 700 nm owing to emission of mercury atom, mercury diatomic molecule, mercury halide, dysprosium, etc., only one lamp is sufficient as the light source in a scientific instrument for spectroscopy used for this wavelength region.

DESCRIPTION OF THE PREFERRED EMBODIMENTS

Figure 1:
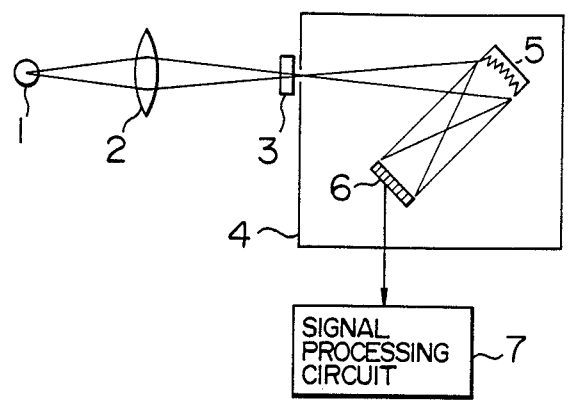
FIGS. 1 and 2 are schematic illustrating two different embodiments of this invention.

Hereinbelow an embodiment of this invention will be explained, referring to FIG. 1. In FIG. 1, reference numeral 1 represents a metal halide lamp containing dysprosium halide; 2 a lens; 3 a sample cell; 4 a monochromator; 5 a concave grating; 6 a photodiode array; and 7 a circuit for signal processing. Light emitted by the metal halide lamp 1 is focused on the entrance slit of the monochromator 4 by the lens 2. The sample cell 3 containing a sample to be measured is located just in front of the entrance slit and absorbes light having wavelength corresponding to the sample. Light entering the monochromator 4 after having passed through the sample cell 3 is dispersed by the concave grating 5 and focused on the photodiode array 6, depending on the wavelength. The wavelength region of the light focused on the photodiode array 6 extends from 220 nm to 700 nm and the absorption spectrum at this wavelength region can be measured at the same time. Heretofore it was not possible because of the fact that there were no suitable light sources emitting light of wide wavelength region extending from the ultraviolet to the visible light, but according to this embodiment it is possible to carry out instantaneously measurements for a wide wavelength region extending from the ultraviolet to the visible light. In addition, when this instrument for spectroscopy is used as a detector for the liquid chromatography, this feature brings a greater effect. That is, in this case, the sample cell 3 is a flow cell for the liquid chromatography. In the liquid chromatography, since the sample passing through the detector varies with the time, measurements should be effected instantaneously for the whole wavelength region. While heretofore only ultraviolet measurements by means of a deuterium discharge lamp could be carried out, according to this embodiment a three-dimensional chromatogram (chromatogram indicating variations in absorption spectra with the time) in a wide wavelength region extending from the ultraviolet to the visible light can be easily obtained.

Figure 2:
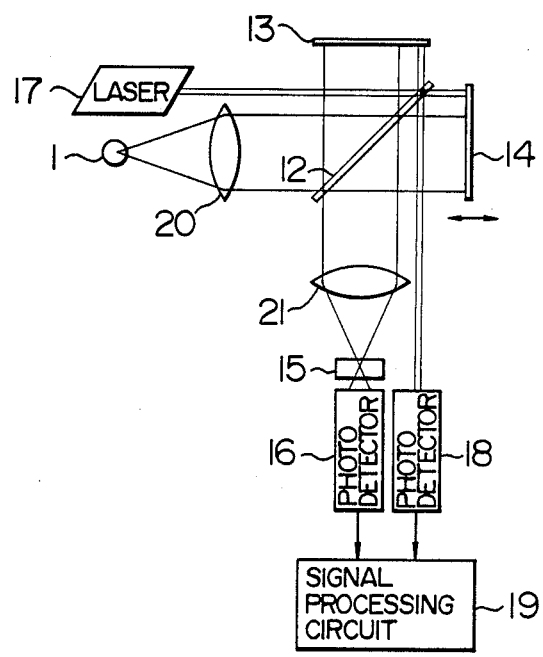

FIG. 2 indicates another embodiment of this invention, in which this invention is applied to a Fourier transform spectroscope. In FIG. 2, the light source 1 is a metal halide lamp containing dysprosium halide and reference numeral 12 indicates a beam splitter; 13 a fixed mirror; 14 a moving mirror; 15 a sample cell; 16 and 18 photodetectors; 17 a laser device; 19 a circuit for signal processing; 20 and 21 lenses. Light emitted by the light source, which is a metal halide lamp, is transformed into a parallel light beam by the lens 20 and divided in two directions by the beam splitter 12. One of the light beams is reflected by the fixed mirror 13 and returned to the beam splitter 12. The other light beam is reflected by the moving mirror 14 and returned to the beam splitter 12. These light beams interfere with each other, focused by the lens 21, and enter the light detector 16 after having passed through the sample cell 15. In order to monitor the position of the moving mirror 14, light emitted by the laser device 17 is made interfere in the similar manner and the interfered light is projected to the light detector 18. That is, signals coming from the light detector 16 are got into the circuit for signal processing 19, triggered by the interfered signal of the laser light due to the movement of the moving mirror 14. The spectroscope is so constructed that, after the data have been taken-in, they are Fourier-transformed in the circuit for signal processing 19 in order to obtain the absorption spectrum. With such a Fourier transform spectroscope the wavelength region, for which measurements can be carried out, depends on the emission spectrum of the light source. Consequently, according to this embodiment, it is possible to realize a Fourier transform spectroscope, by which measurements can be effected for a wide wavelength region extending from the ultraviolet to the visible light, which was not possible heretofore.

Further, as another embodiment, it can be so constructed that the absorption spectrum of the sample is measured, while rotating mechanically the grating and using as the light source a metal halide lamp containing dysprosium halide. According to this construction, a spectroscope can be realized, which has advantages that because the light source is not changed over, the mechanism is simple and cheap with respect to the prior art system, by which a deuterium discharge lamp and a tungsten lamp are changed over, depending on the wavelength region and further that there is no step in the measured values due to the change over of the light source.

Figure 3:
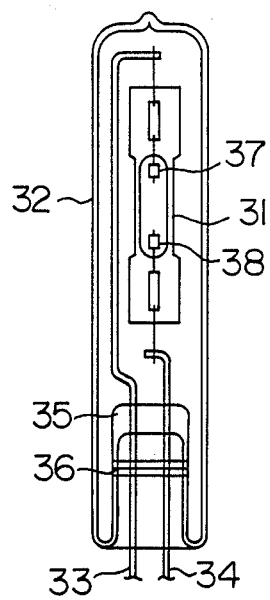
FIG. 3 is a cross-sectional view of an example of the metal halide lamp, which can be used in order to realize this invention.
Figure 4:
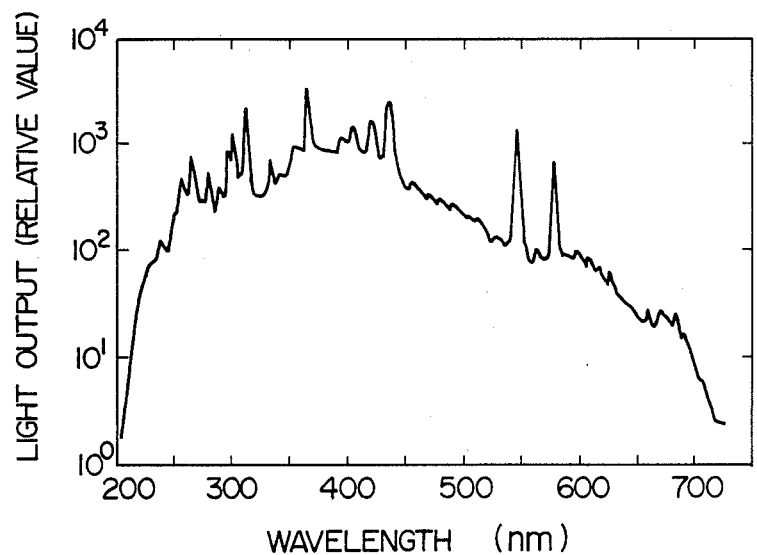
FIG. 4 is a scheme indicating a measurement result of the emission spectrum of the lamp shown in FIG. 3.

FIG. 3 shows an embodiment of the metal halide lamp used for realizing this invention. An arc tube 31 made of fused silica is fixed within an outer bulb made of fused silica. Lead wires 33 and 34 connect electrically a pair of main electrodes 37 and 38 disposed in the arc tube 31, respectively, with a power source (not shown in the figure). The stem portion 35 is made of a kind of glass having a great coefficient of expansion and permitting to seal the lead wires 33 and 34 and jointed through a connecting glass with the outer bulb 32 made of fused silica. The inner volume of the arc tube 31 is about 0.3 $cm^3$ and the distance between the main electrodes 37 and 38 is 10 mm. Mercury, dysprosium, mercury iodide, and inert gas for starting are enclosed in the arc tube 31 to fabricate the lamp. After the fabrication the lamp is left for several hours in an electric furnace or operated for several hours. Then dysprosium having a low vapor pressure reacts with iodine and is transformed into dysprosium iodide having a high vapor pressure so that it can contributes to light emission due to discharge. FIG. 4 shows a measurement result of the emission spectrum of a metal halide lamp fabricated in this way. It is shown there that it has a strong spectrum for a wide wavelength region extending from about 220 nm to about 700 nm.

As explained above, according to this invention, since it is possible to carry out measurements for a wide wavelength region extending from the ultraviolet to the visible light with a single light source, effects can be obtained that it is not necessary to change over the light source and the mechanism is made simpler and cheaper and further that there is no step in the measured values due to the change over of the light source and thus measurements can be effected with a high reliability.

What is claimed is:

1. An instrument for spectroscopy comprising:

a light source provided with a metal halide lamp containing mercury and dysprosium halide;

spectroscopic means for dispersing light from said light source over a wavelength region extending at least from 220 to 700 nm;

detector means for detecting the amount of the light, which has passed through said spectroscopic means;

means for signal processing, which treats detected output signals coming from said detector means; and means for locating a sample to be measured in the light path from said light source to said detector means.

* * * * *